United States Patent
Hell et al.

(10) Patent No.: US 6,897,263 B2
(45) Date of Patent: May 24, 2005

(54) BETAINE ESTERS

(75) Inventors: Kerstin Hell, Essen (DE); Philipp Tomuschat, Essen (DE); Bernd Weyershausen, Essen (DE)

(73) Assignee: Goldschmidt AG, Essen (DE)

( * ) Notice: Subject to any disclaimer, the term of this patent is extended or adjusted under 35 U.S.C. 154(b) by 198 days.

(21) Appl. No.: 10/184,370

(22) Filed: Jun. 28, 2002

(65) Prior Publication Data

US 2003/0108513 A1 Jun. 12, 2003

(30) Foreign Application Priority Data

Jul. 3, 2001 (DE) .......................... 101 32 173

(51) Int. Cl.[7] .................. C08F 283/04; C08G 69/48
(52) U.S. Cl. .................. 525/420; 528/271; 528/272; 528/422; 528/425; 525/329.4; 525/329.7; 525/330.3; 252/175; 510/504
(58) Field of Search ................ 528/271, 272, 528/422, 425; 525/329.4, 329.7, 330.3, 420; 252/175; 510/504

(56) References Cited

U.S. PATENT DOCUMENTS 5,958,870 A 9/1999 Declercq et al.

FOREIGN PATENT DOCUMENTS

| DE | 35 27 974 A1 | 2/1987 |
|---|---|---|
| DE | 43 09 567 A1 | 9/1994 |
| EP | 0 367 939 A1 | 5/1990 |
| EP | 0 507 003 A2 | 10/1992 |
| EP | 0 771 785 A1 | 5/1997 |
| EP | 0 799 885 A1 | 10/1997 |
| WO | WO 96/38528 | 12/1996 |

*Primary Examiner*—Samuel A. Acquah
(74) *Attorney, Agent, or Firm*—Scully, Scott, Murphy & Presser

(57) ABSTRACT

The invention relates to compounds of the general formula (I)

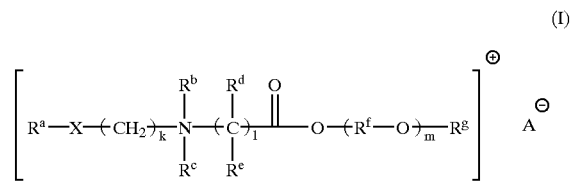

in which $R^a$ is an ethylenically unsaturated radical having 1 to 5 carbon atoms and containing at least one carbonyl function, and to their homopolymers and copolymers with compounds of the general formula (II)

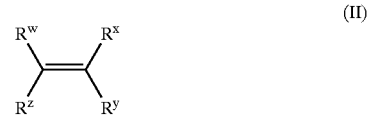

and to the use thereof in hair conditioning agents.

7 Claims, No Drawings

BETAINE ESTERS

DESCRIPTION

1. Field of the Invention

The present invention relates to novel polymerizable betaine esters and to polymers preparable therefrom.

2. Background of the Invention

The regular washing of hair using degreasing surfactants and the frequent bleaching, permanent waving and coloring thereof leads to damage to the hair structure. Despite the potential for hair structure damage, hair treatment agents or conditioning agents with combability-improving and care properties have achieved considerable importance. Moreover, esthetic factors, such as, for example, odor, play and ever more important role. For this reason, a perfume oil is used in addition to the conditioning components in many hair care formulations.

Hair conditioning formulations serve for the protection against hair damage, the symptomatic repair of hair damage and the concealment of hair damage. Hair conditioning agents generally used in such formulations are cationic or aminofunctional substances. These substances can interact with anionic centers on the surface of the hair and attach substantively to this surface.

Customary conditioning agents include, for example, cetyltrimethylammonium salts, distearyldimethylammonium salts, fatty acid esters of triethanolmethylammonium salts, methylated imidazolinium salts and other products. Betaine esters are also proposed for use in hair care and body care, and also cleaning products. Betaine esters are reportedly used, inter alia, for the preparation of particularly mild hair and skin conditioning agents, and shampoos, see, for example, DE-A-35 27 974, DE-A-43 09 567, EP-A-0 367 939 or EP-A-0 507 003. However, betaine esters are considered to be less effective in regard to their conditioning properties compared with the abovementioned customary conditioning agents.

It is known that cationic or amino functional conditioning agents have to be converted to a cosmetically/odorously acceptable formulation through the use of perfume oils. However, after a prolonged period following use of the conditioning formulation, the effect of perfume oil decreases and the fat-like and or aminic odor of the conditioning agent has a negative effect.

In view of the above problem with prior art betaine esters, there is a need to provide new and improved betaine esters which exhibit good attachment behavior to hair, while providing a long-lasting and pleasing scent to hair.

SUMMARY OF THE INVENTION

An object of the present invention is to provide novel betaine esters or betaine ester polymers which, as well as having good attachment behavior to hair, impart a long-lasting pleasant scent to the hair. Surprisingly, the compounds according to the present invention additionally have very good conditioning properties. Even the non-fragrace alcohol-functionalized polymeric betaine esters of the present invention have conditioning properties associated therewith.

The present invention therefore provides polymerizable betaine esters of general formula (I)

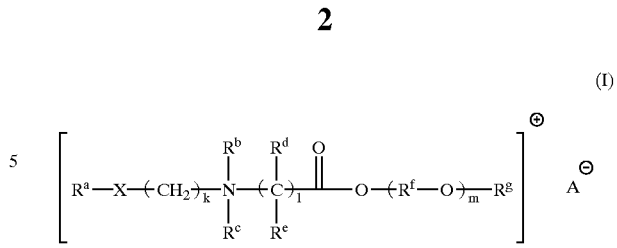

in which $R^a$ is an ethylenically unsaturated radical containing at least one carbonyl function, such as, for example, acryloyl, methacryloyl, maleinoyl or itaconoyl;

X is an oxygen atom, —N(CH$_3$)— or —NH—;

$R^b$ and $R^c$, independently of one another, are optionally branched alkyl radicals having 1 to 4 carbon atoms, which radicals may also contain heteroatom substituents, in particular O, S, N, or P;

$R^d$ and $R^e$, independently of one another, are chosen from hydrogen (H), optionally branched alkyl radicals having 1 to 4 carbon atoms, optionally substituted aryl or benzyl radicals, and —CH$_2$COOH, —CH$_2$COOR$^1$, —CH$_2$CH$_2$COOH, —CH$_2$CH$_2$COOR$^1$, where $R^1$ is a short chain alkyl having 1–4 carbon atoms;

$R^f$ is an optionally multiple bond-containing branched and/or substituted and/or cyclic hydrocarbon radical having 1 to 10, preferably 2 or 3, carbon atoms, a styrene radical, a group derived exclusively from ethylene or propylene radicals or butylene or styrene radicals, or a block copolymer or random copolymer containing said radicals;

$R^g$ is an optionally branched, optionally double bond-containing, optionally cyclic hydrocarbon radical having 1 to 22 carbon atoms, with the proviso that when m=0, $R^g$ is an optionally branched, optionally double bond-containing hydrocarbon radical and when m is >0, $R^g$ may be H;

k and l, independently of one another, are 1 to 4, where k is preferably 2 or 3 and l is preferably 1;

m has a value between 0 and 100, preferably 0 and 40; and

A$^-$ is an anion, such as, for example, a halogenide, an alkylsulfate or an alkylsulfonate.

The present invention further relates to homopolymers prepared from polymerizable betaine esters of general formula (I), and also copolymers prepared from polymerizable betaine esters of general formula (I) and suitable comonomers of general formula (II)

in which $R^x$ and $R^y$ are H, $R^w$ is H or CH$_3$, and $R^z$ is a radical containing at least one carbonyl group, such as, for example, —C(O)OR, —C(O)NR'R", where R, R' and R" are H or optionally multiple bond-containing, linear or branched and/or cyclic and/or substituted and/or halogen atom-containing and/or heteroatom-containing and/or carbonyl group-containing hydrocarbon radicals having 1 to 18 carbon atoms;

or in which $R^w$ and $R^z$ are H, $R^y$ and $R^z$ are radicals containing a carbonyl group, such as, for example, —C(O)OR, —C(O)NR'R", where R, R' and R" are H or optionally multiple bond-containing, linear or branched and/or cyclic aliphatic or aromatic and/or substituted and/or halogen atom and/or heteroatom-containing hydrocarbon radicals having 1 to 18 carbon atoms;

or in which $R^w$, $R^x$ and $R^y$ are H and $R^z$ is an optionally halogen atom- and/or heteroatom-substituted, linear and/or branched alkyl substituent-containing aromatic or heteroaromatic;

or in which $R^w$, $R^x$ and $R^y$ are H and $R^z$ is —$(CH_2)_3$—$OR'''$, where $R'''$ is H, an optionally carbonyl group-containing alkyl radical having 1 to 22 carbon atoms or a polyether derived exclusively from ethylene oxide or propylene oxide, or butylene oxide or styrene oxide, which represents a block or random copolymer containing said radicals, and a is 0 or 1.

Suitable comonomers, which can be employed in the present invention, are chosen, for example, from the following representative groups:

ethylenically unsaturated carboxyl group-containing compounds, such as, for example, acrylic acid, methacrylic acid, maleic acid, maleic anhydride, maleic mono- and diesters of itaconic acid;

$C_1$–$C_{18}$-acrylic esters, methacrylic esters or maleic mono- or diesters, such as, for example, methyl acrylate, ethyl acrylate, propyl acrylate, n-butyl acrylate, i-propyl acrylate, t-butyl acrylate, n-hexyl acrylate, methyl methacrylate, ethyl methacrylate, propyl methacrylate, i-propyl methacrylate, n-butyl methacrylate, n-hexyl methacrylate, n-dodecyl methacrylate;

polyethylene glycol and polypropylene glycol acrylates and methacrylates;

$C_2$–$C_{18}$-alkoxy esters of acrylic and methacrylic acid, such as, for example, methoxyethyl acrylate, ethoxyethyl acrylate, methoxyethyl methacrylate, ethoxyethyl methacrylate, methoxybutyl acrylate, methoxybutyl methacrylate, ethoxybutyl acrylate, ethoxybutyl methacrylate;

$C_2$–$C_8$-hydroxyalkyl acrylates and methacrylates, such as, for example, hydroxyethyl acrylate, hydroxyethyl methacrylate, hydroxypropyl acrylate, hydroxypropyl methacrylate, hydroxybutyl acrylate, hydroxybutyl methacrylate;

vinyl compounds, such as, for example, styrene, α-methylstyrene, vinyl toluene, p-chlorostyrene, vinyl esters, such as vinyl acetate and also vinyl ether, vinyl polyether, vinyl alcohol, halogenated vinyl compounds, allyl vinyl ketone, 4-vinylpridine, N-vinylpyrrolidone, vinylimidazole;

amides of acrylic acid and methacrylic acid, such as, for example, methacrylamide, N,N-dimethylacrylamide, N,N-dimethylmethacrylamide, N,N-dimethylaminopropylacrylamide, N,N-dimethylaminopropylmethacrylamide;

diallyldimethylammonium chloride (DADMAC); and allyl polyethers.

The above list of comonomers does not, however, represent any limitation with regard to suitable comonomers that can be employed in the present invention.

Surprisingly, it has now been found that the novel polymerizable betaine esters and polymeric betaine esters according to the present invention which, in the case of the homopolymers, are prepared from the monomeric polymerizable betaine esters of general formula (I), and in the case of the copolymers, are prepared by polymerizable betaine esters of general formula (I) and suitable comonomers of general formula (II), have conditioning properties. In embodiments where fragrance alcohol-functionalized betaine ester polymers are employed, these betaine ester compounds have a surprisingly pleasant odor associated therewith.

DETAILED DESCRIPTION OF THE INVENTION

Compounds of the General Formula (I)

The inventive monomeric, polymerizable betaine esters of general formula (I) represent novel substances that can be prepared using known methods of the prior art which are typically employed for preparing such prior art betaine esters. Monomeric betaine esters of general formula (I) can then be free-radically homo- or copolymerized by known methods of the prior art using customary initiators, such as potassium peroxodisulfate or diazo compounds (see, for example, D. Braun, H. Cherdron, H. Ritter, Pratikum der Makromolekularen Stoffe, Wiley-VCH, Weinheim, 1999).

The procedure generally involves, in a first step, esterifying the halocarboxylic acid, preferably monochloroacetic acid (10–100% excess, preferably 10%) with the corresponding alcohol component HO—$(R^f$—$O)_m$—$R^g$, optionally using a catalyst, by heating the two reactants under a nitrogen atmosphere to 80° to 200° C., preferably 100° to 140° C., particularly preferably about 120° C. The water of reaction that forms is continuously distilled off during the process using a distillation bridge. The esterification generally lasts about three hours and the esterification process is terminated when the water of reaction no longer distills off. The excess monochloroacetic acid is then removed by distillation in vacuo at pressures of, preferably, less than 1 mbar. The purity of the products is checked, inter alia, via the content of chlorine and NMR spectroscopy. In the second step, ethylenically unsaturated carboxylic acid amidoamines are quaternized with the monochloroacetic ester. For this purpose, the monochloroacetic ester is preferably heated together with an amidoamine of the formula $R^a$—NH—$(CH_2)_k$—$NR^bR^c$ in the presence of from 0.01% by weight to 0.5% by weight, preferably 0.1% by weight, of a free-radical scavenger (inhibitor) under a nitrogen atmosphere for approximately three to six, preferably four, hours at 40° to 80° C., preferably 60° C.

The homopolymerization of betaine esters is generally carried out as follows: firstly, the betaine ester is initially introduced under a nitrogen atmosphere, and a solvent, preferably water or isopropanol, is added. The mixture is then heated to a temperature of from 60° to 120° C., preferably 800 to 100° C., particularly preferably 90° C. in the case of water as solvent, and 80° C. in the case of isopropanol as solvent, to slowly and completely dissolve the betaine ester.

If water is used as solvent, after the reaction temperature has been reached, 1 to 5 mol %, preferably 2 mol %, of a water-soluble free-radical initiator, preferably potassium peroxodisulfate, dissolved in water, are added dropwise with stirring over a period of from 0.5 to 2 hours, preferably 1 hour. The mixture is then stirred for a further 1 to 4 hours, preferably 2 hours at the corresponding temperature, and the water is then distilled off in vacuo.

If isopropanol is used as solvent, after the reaction temperature has been reached, 0.05 to 0.5 mol %, preferably 0.1 to 0.2 mol %, of a diazo free-radical initiator, dissolved in isopropanol, are added dropwise with stirring over a period of from 1 to 5 hours, preferably 2 hours. The mixture is then stirred for a further 1 to 3 hours at the reaction temperature. Then, to complete the polymerization, one to three times, preferably one and a half times, the amount of diazo free-radical initiator, based on the first addition, dissolved in isopropanol, is added dropwise over a period of from 0.5 to 1.5 hours, preferably 30 to 45 minutes, and the mixture is stirred for a further 1 to 3 hours, preferably 2 hours, at the reaction temperature. Irrespective of the solvent used, when the reaction is complete, the solvent is distilled off in vacuo.

Copolymerizations are carried out in a solvent, preferably in isopropanol, under a protective gas atmosphere. In accordance with the present invention, the solvent is initially introduced and solutions of the comonomers are added dropwise to the reaction vessel at the same time. In this regard, the free-radical initiator, preferably a diazo compound, is dissolved in one of the solutions which comprises one of the comonomers. Otherwise the reaction conditions are analogous to those for the homopolymerization with diazo compounds.

According to the present invention, preference is given to compounds in which the radical $R^a$ is —C(O)—CH=CH$_2$ and in particular the radicals $R^b$ and $R^c$ are both —CH$_3$ and the radicals $R^d$ and $R^e$ are both H, and/or compounds in which k=2 or 3 and l=1, and/or compounds in which m=0, preferably compounds in which $R^a$ is —C(O)—CH=CH$_2$, R and $R^c$ are —CH$_3$, $R^d$ and $R^e$ are simultaneously H, $R^f$ is an ethylene radical or propylene radical and k=3, l=1, m=0 to 40 and $R^g$ is an alkyl radical having 1 to 22 carbon atoms or hydrogen.

Preference is also given to compounds of general formula (I) in which $R^f$ may be a styrene or butylene radical or, preferably, a propylene radical, with particular preference given to compounds of general formula (I) in which $R^f$ is an ethylene radical where $R^f$ may be constructed exclusively from ethylene or propylene or butylene or styrene radicals, or else a block copolymer or random copolymer containing said radicals, and/or compounds in which $R^g$ is an alkyl radical or alkenyl radical having 8 to 18 carbon atoms, such as, preferably, the radical of a fatty alcohol based on natural fatty acids which can be prepared by known processes, and/or compounds in which m=0 and $R^g$ is a fragrance alcohol.

For the purposes of the present invention, fragrance alcohols that can be used are all "active alcohols" which, when incorporated into formulations in concentrations of from about 0.01 to about 10% by weight, impart a pleasant scent thereto. Compounds of this type are described, for example, in EP-A-0 799 885, EP-A-0 771 785, WO 96/38528 (PCT/US96/06758), U.S. Pat. No. 5,958,870. From this class of alcohols, preference is given in the present invention to co-using the following fragrance alcohols: 2-phenoxyethanol, phenylethyl alcohol, geraniol, citronellol, hydroxycitronellol, farnesol, menthol, eugenol, vanillin, ethylvanillin, cis-3-hexenol, nerol, (x-terpineol, linalool, tetrahydrolinalool, 1,2-dihydromyrcenol, 3-methyl-5-phenyl-1-pentanol, 2,4-dimethyl-3-cyclohexene-1-methanol. However, the above list of alcohols does not represent any limitation with regard to suitable fragrance alcohols that can be employed in the present invention.

The fatty acids co-used for the preparation of fatty alcohols are, individually or in mixtures, fatty acids such as caproic acid, caprylic acid, capric acid, 2-ethylhexanoic acid, lauric acid, myristic acid, palmitic acid, palmitoleic acid, isostearic acid, stearic acid, hydroxystearic acid (ricinoleic acid), dihydroxystearic acid, oleic acid, linoleic acid, petroselic acid, elaidic acid, arachidic acid, behenic acid, erucic acid, gadoleic acid, and the technical-grade mixtures which form during the pressurized cleavage of natural fats and oils, such as oleic acid, linoleic acid, linolenic acid, and in particular rapeseed oil fatty acid, soybean oil fatty acid, sunflower oil fatty acid, tallow oil fatty acid. In principle, all fatty acids with a similar chain distribution are suitable for use in the present invention.

The content of unsaturated fractions in these fatty acids or fatty acid esters is, where necessary, adjusted by the known catalytic hydrogenation processes to a desired iodine number, or is achieved by mixing completely hydrogenated fatty components with nonhydrogenated fatty components.

The iodine number, being a measure of the average degree of saturation for a fatty acid, is the amount of iodine that is taken up by 100 g of the compound to saturate the double bonds.

Preference is given to using partially hydrogenated $C_8/C_{18}$-coconut or palm fatty acids, rapeseed oil fatty acids, sunflower oil fatty acids, soybean fatty acids and tallow oil fatty acids, having iodine numbers in the range from about 80 to 150 and, in particular, technical-grade $C_8/C_{18}$-coconut fatty acids, where a selection of cis/trans isomers, such as $C_{16/18}$-fatty acid cuts rich in elaidic acid may be advantageous. Such fatty acids are commercially available products and are supplied by various companies under their respective trade names.

The novel betaine esters of general formula (I) to be used according to the present invention, but, in particular, the homo- and copolymers preparable therefrom, can, for example, be used for the preparation of hair conditioning agents, in particular for the preparation of hair shampoos, hair cures, hair rinses and the like. The betaine esters of the present invention positively influence sensory test parameters such as, for example, wet combability, and, depending on the type of employed polymer based on betaine esters of general formula (I) and suitable comonomers of general formula (II), test parameters such as, for example, shine or volume can also be positively influenced.

The betaine esters of the present invention can also be used outside of cosmetic productssince the compounds are cleavable upon changes in pH. The cleavability of the inventive betaine esters may result in the formation of switch surfactants with the possibility of targeted activation or deactivation.

Betaine esters of general formula (I) are likewise of particular interest for the cleaning of motor vehicles in automatic car washes since after the motor vehicle washing, the wash lye is heavily contaminated with oil residues and an oil separator has to be used. In this regard, the pH-controlled cleavability of the betaine esters is likewise advantageous.

Because of their cationic character, betaine esters of general formula (I) can be used in floor care products for PVC and other plastic floors, where the betaine ester increase the shine and at the same time can be removed again during the next application in order to avoid the build up of layers on the floor surface.

The following examples are given to illustrate the preparation of the inventive betaine esters as well as to show some advantages that can be obtained in using the inventive betaine esters.

In the following examples, the amounts of starting materials for the preparation of the chloroacetic ester are calculated on the basis of the OH numbers determined from the alcohols to be used. This applies in particular to the polyethers used as alcohol component. The purity of the chloroacetic esters is determined by means of NMR spectroscopy, acid number and the percentage chlorine content in the product.

The amount of chloroacetic ester to be used for the preparation of the betaine esters is calculated on the basis of the chlorine content. To prepare the ethylenically unsaturated betaine esters of the general formula (I) according to the invention, commercial N-(3-N',N'-dimethylaminopropyl)acrylamide is preferably used (reference source Aldrich, 97%, CAS 3845-76-9).

Preparation of Ethylenically Unsaturated Carboxylic Acid Amidoamine Betaine Esters I. cis-3-Hexenyl chloroacetate 10 g (0.1 mol) of cis-3-hexenol were heated together with 10.4 g (0.11 mol) of chloroacetic acid at 120° C. for 2 h under a nitrogen atmosphere in a 250 ml four-necked flask fitted with stirrer, thermometer and distillation bridge. The temperature was then increased to 130° C. and the mixture was stirred for an additional two hours. The water of reaction which formed during the reaction was continuously removed from the reaction mixture by distillation. After a total reaction time of 4 h, a vacuum of 0.1 mbar was applied in order to remove excess chloroacetic acid. 17.6 g (0.1 mol) of a yellowish liquid were obtained.

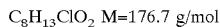

$C_8H_{13}ClO_2$ M=176.7 g/mol

Acid number: 9 mg (KOH)/g (product), this corresponds to 0.22% Cl from the free chloroacetic acid. For an overall chlorine content of 20.1%, this corresponds to a conversion of 99%.

$^1$H-NMR (400 MHz, CDCl$_3$): δ=0.96 (t, $^3J_{HH}$=7.53 Hz, 3H, CH$_3$), 2.03 (pseudo quintet, $J_{HH}$=7.36 Hz, 2H, H-5'), 2.39 (pseudo quartet, $J_{HH}$=7.05 Hz, 2H, H-2'), 4.03 (s, 2H, H-2), 4.15 (t, $^3J_{HH}$=6.93 Hz, 2H, H-1'), 5.27 (m, 1H, vinylic H), 5.49 (m, 1H, vinylic H) ppm.

$^{13}$C-NMR (100.6 MHz, CDCl$_3$): δ=13.52 (1C, CH$_3$), 19.97 (1C, CH$_2$), 25.92 (1C CH$_2$), 40.32 (1C, CH$_2$Cl), 65.03 (1C, CH$_2$O), 122.54 (1C, C=C), 134.27 (1C, C=C 166.89 (1C, C=O) ppm.

II. N-(3-Acrylamidopropyl)-N,N-dimethyl-N-(cis-3-hexenyloxycarbonyl)methylammonium chloride 17.6 g (0.1 mol) cis-3-hexenyl chloroacetate were weighed into a 250 ml four-necked flask fitted with stirrer, thermometer and reflux condenser. Following the addition of 0.02 g (0.1%) of p-methoxyphenol, the mixture was heated, with stirring, to the reaction temperature of 60° C., and then 15.6 g (0.1 mol) of N-(3-N',N'-dimethylaminopropyl)acrylamide were slowly added dropwise. During this addition, a slight exothermic reaction was observed, while in the further course of the reaction, the temperature was maintained at 60° C. by adding the acrylamidoamine. When the addition of the acrylamidoamine was complete, the mixture was stirred for an additional 4 h at 60° C., during which a clear increase in the viscosity was observed. The product was in the form of a brown high-viscosity mass.

$C_{16}H_{29}ClN_2O_3$ M=332.92 g/mol

Total chlorine content: 10.6%, of which chloride: 10.1%, this corresponds to a conversion of 93%.

$^1$H-NMR (400 MHz, D$_2$O): δ=0.79 (t, $^3J_{HH}$=7.51 Hz, 3H, CH$_3$), 1.84–1.96 (m, 4H), 2.31 (pseudo quartet, $^3J_{HH}$=6.29 Hz, 2H, CH$_2$), 3.20–3.26 (m, 2H, NHCH$_2$), 3.31 (s, 6H, N(CH$_3$)$_2$), 3.43–3.49 (m, 2H, NCH$_2$), 4.13 (t, $^3J_{HH}$=6.5 Hz, 2H, CH$_2$O), 4.15 (s, 2H, NCH$_2$C(O)), 5.19–5.27 (m, 1H, vinylic H), 5.43–5.51 (m, 1H, vinylic H), 5.64 (dd, $^2J_{HH}$=9.52 Hz, $^3J_{HH}$=2.05 Hz, 1H, vinylic H), 6.05–6.16 (m, 1H, vinylic H) ppm.

$^{13}$C-NMR (100.6 MHz, D$_2$O): δ=14.09, 20.63, 22.87, 26.29, 36.33, 52.58, 55.73, 61.67, 63.35, 67.0, 124.22, 128.1, 130.24, 136.03, 165.41, 169.04 ppm.

III. 3,7-Dimethyloct-6-en-1-yl chloroacetate, citronellol chloroacetate 15.6 g (0.1 mol) of citronellol were heated together with 10.4 g (0.11 mol) of chloroacetic acid at 120° C. for 3 h under a nitrogen atmosphere in a 250 ml four-necked flask fitted with stirrer, thermometer and distillation bridge. The temperature was then increased to 130° C. and the mixture was stirred for an additional two hours. The water of reaction which formed during this reaction was removed continuously from the reaction mixture by distillation. After a total reaction time of 4 h, a vacuum of 0.1 mbar was applied in order to remove excess chloroacetic acid. 22.3 g (0.096 mol) of a yellowish liquid were obtained.

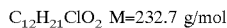

$C_{12}H_{21}ClO_2$ M=232.7 g/mol

Acid number: 8.4 mg (KOH)/g (product), this corresponds to 0.0061% Cl from the free chloroacetic acid For a total chlorine content of 15.2%, this corresponds to a conversion of 96%.

$^1$H-NMR (400 MHz, CDCl$_3$): δ=0.90 (d, $^3J_{HH}$=6.56 Hz, 3H, CH$_3$), 1.11–1.22 (m, 1H), 1.27–1.37 (m, 1H), 1.41–1.50 22 (m, 1H), 1.53 (pseudo quartet, $J_{HH}$=6.51 Hz, 1H), 1.58 (s, 3H, CH$_3$), 1.66 (s, 3H, CH$_3$), 1.65–1.73 (m, 1H), 1.87–2.03 (m, 2H), 4.02 (s, 2H, H-2), 4.15–4.26 (m, m, 2H, H-1'), 5.06 (m, 1H, vinylic H) ppm.

$^{13}$C-NMR (100.6 MHz, CDCl$_3$): δ=16.91 (1C, CH$_3$), 18.69 (1C, CH$_2$), 24.73 (1C, CH$_3$), 24.99 (1C, CH$_3$), 28.72 (1C), 34.66 (1C), 36.29 (1C), 40.26 (1C, CH$_2$Cl), 63.98 (1C, CH$_2$O), 123.89 (1C, C=C), 130.48 (1C, C=C), 161.71 (1C, C=O ppm.

IV. N-(3-Acrylamidopropyl)-N,N-dimethyl-N-(3,7-dimethyloct-6-en-1-oxycarbonyl)methylammonium chloride 22 g (0.094 mol) of citronellol chloroacetate were weighed into a 250 ml four-necked flask fitted with stirrer, thermometer and reflux condenser. Following the addition of 0.02 g (0.1%) of p-methoxyphenol, the mixture was heated, with stirring, to the reaction temperature of 60° C., and then 14.7 g (0.094 mol) of N-(3-N',N'-dimethylaminopropyl)acrylamide were slowly added dropwise. During this addition, a slight exothermic reaction was observed, where in the further course of the reaction the temperature was maintained at 60° C. by adding the acrylamidoamine. When the addition of the acrylamidoamine was complete, the mixture was stirred for an additional 4 h at 60° C., during which a significant increase in the viscosity was observed. The product was in the form of a high-viscosity mass.

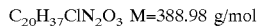

$C_{20}H_{37}ClN_2O_3$ M=388.98 g/mol

Total chlorine content: 9.1%, of which chloride: 8.7%, this corresponds to a conversion of 96%.

$^1$H-NMR (400 MHz, CDCl$_3$): δ=0.87 (d, $^3J_{HH}$=6.75 Hz, 3H, CH$_3$), 1.09–1.20 (m, 1H), 1.24–1.34 (m, 1H), 1.38–1.51 (m, 2H), 1.56 (s, 3H, CH$_3$), 1.64 (s, 3H, CH$_3$), 1.60–1.68 (m, 1H), 1.84–2.0 (m, 2H), 3.36–3.44 (m, 2H), 3.47 (s, 6H, N(CH$_3$)$_2$), 4.05–4.12 (m, 2H), 4.15–4.23 (m, 2H, CH$_2$O), 4.6 (s, 2H, NCH$_2$C(O)), 5.0–5.06 (m, 1H, vinylic H$_{citronellol}$), 5.55 (dd, $^3J_{HH}$=10.11 Hz, $^3J_{HH}$=2.04 Hz, 1H, vinylic H-2), 6.24 (dd, $^2J_{HH}$=17.05 Hz, $^3J_{HH}$=2.04 Hz, 1H, vinylic H-3a), 6.42 (dd, $^2J_{HH}$=17.05 Hz, $^3J_{HH}$=10.67 Hz, 1H, vinylic H-3b), 8.47 (t, $^3J_{HH}$=5.57 Hz, 1H, NH) ppm.

$^{13}$C-NMR (100.6 MHz, CDCl$_3$): δ=16.4 (1C, CH$_3$), 18.02, 21.52 ($^+$NCH$_2$CH$_2$CH$_2$NC(O)), 23.96 (1C, CH$_3$), 24.45 (1C, CH$_3$), 28.05, 33.72, 34.86 (1C, CH$_2$NHC(O)), 35.53, 50.1 (2C, N(CH$_3$)$_2$), 59.96, 62.33, 64.0 (CH$_2$O), 122.97, 124.36 (C-2), 130.0, 130.14 (C-3), 163.30, 164.96 ppm.

V. N-(3-Acrylamidopropyl)-N,N-dimethyl-N-(lauryl-PEG9-oxycarbonylmethyl)ammonium chloride 65.74 g (0.1 mol) of lauryl-PEG9 chloroacetate were weighed into a 250 ml four-necked flask fitted with stirrer, thermometer and reflux condenser. Following the addition of 0.07 g (0.1%) of p-methoxyphenol, the mixture was heated, with stirring, to the reaction temperature of 60° C., and then 15.6 g (0.1 mol) of N-(3-N',N'-dimethylaminopropyl) acrylamide were slowly added dropwise. During this addition, a slight exothermic reaction was observed, wherein the further course of the reaction the temperature was maintained at 60° C. by adding the acrylamidoamine. When the addition of the acrylamidoamine was complete, the mixture was stirred for an additional 4 h at 60° C., during which a significant increase in the viscosity was observed. The product was a high-viscosity yellow mass.

$C_{40}H_{79}ClN_2O_{11}$ M=799.52 g/mol

Total chlorine content: 4.4%, of which chloride: 4.3%, this corresponds to a conversion of 98%.

$^1$H-NMR (400 MHz, CDCl$_3$): δ=0.84 (t, $^3J_{HH}$=6.79 Hz, 3H, CH$_3$), 1.17–1.30 (m, 18H), 1.49–1.57 (m, 2H, CH$_2$), 1.98–2.16 (m, 2H, CH$_2$), 3.36–3.47 (m, 10H, CH$_2$, NHCH$_2$, N(CH$_3$)$_2$), 3.50–3.55 (m, 2H, CH$_2$), 3.56–3.64 (m, 30H), 3.65–3.70 (m, 2H, CH$_2$), 3.99–4.09 (m, 2H, NCH$_2$), 4.26–4.38 (m, 2H, CH$_2$O), 4.59–4.66 (m, 2H, NCH$_2$C(O)), 5.52–5.58 (m, 1H, vinylic H), 6.2–6.28 (m, 1H, vinylic H), 6.42 (dd, $^2J_{HH}$=17.05 Hz, $^3J_{HH}$=10.67 Hz, 1H, vinylic H), 8.48–8.56 (m, 1H, NH) ppm.

$^{13}$C-NMR (100.6 MHz, CDCl$_3$): δ=13.08 (1C, CH$_3$), 21.56 (1C), 24.98 (1C), 28.23 28.37, 28.50, 28.51, 28.54 (7C), 31.79 (1C), 35.05 (1C), 50.56 (2C), 60.26 (1C), 62.67 (1C), 64.11 (1C), 67.25, 68.95, 69.41, 70.30 (17C), 124.53 (1C), 130.46 (1C), 163.51 (1C), 165.15 (1C) ppm.

VI. Butyl-PPG22**-PEG4* chloroacetate 143.9 g (corresponding 0.1 mol based on the OH number) of butyl-PPG22-PEG4 alcohol and 10.4 g (0.11 mol) of chloroacetic acid were heated in the presence of 0.39 g (2 mmol) of p-toluenesulfonic acid hydrate at 130° C. for 4 h under a nitrogen atmosphere in a 250 ml distillation apparatus. Volatile impurities and excess chloroacetic acid were then removed in vacuo (1 mbar). 150.9 g of a yellow-orange liquid were obtained.

| | |
|---|---|
| *PEG4 = —(CH$_2$—CH$_2$—O)$_4$— | polyethylene glycol |
| **PPG22 = —(CH$_2$—CH(CH$_3$)—O)$_{22}$— | polypropylene glycol |
| $C_{80}H_{159}ClO_{28}$ | M = 1603.7 g/mol |

Acid number: 0.26 mg (KOH)/g (product), this corresponds to 0.042% Cl from the free chloroacetic acid. For a total chlorine content of 2.21%, this corresponds to a conversion of 98%.

$^1$H-NMR (400 MHz, CDCl$_3$): δ=0.87 (t, $^3J_{HH}$=7.19 Hz, 3H, CH$_3$), 1.04–1.14 (m, 66H, PPG-CH$_3$), 1.27–1.37 (m, 2H, CH$_2$), 1.45–1.54 (m, 2H, CH$_2$), 1.98–2.1 (m, 2H, CH$_2$), 2.01 (s, 3H, CH$_3$), 3.25–3.72 (m, 82H), 4.02–4.05 (m, 1H, CH), 4.07 (m, 2H, CH$_2$), 4.29–4.34 (m, 1H, CH) ppm.

VII. N-(3-Acrylamidopropyl)-N,N-dimethyl-N-(butyl-PPG22-PEG4-oxycarbonylmethyl)ammonium chloride 160.4 g (0.1 mol) of (butyl-PPG22-PEG4) chloroacetate were weighed into a 500 ml four-necked flask fitted with stirrer, thermometer and reflux condenser. Following the addition of 0.2 g (0.1%) of p-methoxyphenol, the mixture was heated, with stirring, to the reaction temperature of 60° C. and 15.6 g (0.1 mol) of N-(3-N',N'-dimethylaminopropyl) acrylamide was slowly added dropwise. During this addition, a slight exothermic reaction was observed, wherein the further course of the reaction the temperature was maintained at 60° C. by adding the acrylamidoamine. When the addition of the acrylamidoamine was complete, the mixture was stirred for an additional 4 h at 60° C., during which a significant increase in the viscosity was observed. 176 g of an orange high-viscosity liquid were obtained.

$C_{88}H_{175}ClN_2O_{29}$ M=1759.85 g/mol

Total chlorine content: 2.2%, of which chloride: 2.13%, this corresponds to a conversion of 97%.

$^1$H-NMR (400 MHz, CDCl$_3$): δ=0.88 (t, $^3J_{HH}$=7.51 Hz, 3H, CH$_3$), 1.05–1.15 (m, 66H, PPG-CH$_3$), 1.28–1.38 (m, 2H, CH$_2$), 1.47–1.56 (m, 2H, CH$_2$), 2.04–2.1 (m, 2H, CH$_2$), 3.24–3.70 (m, 92H), 4.0–4.14 (m, 2H), 4.28–4.36 (m, 2H), 4.58–4.64 (m, 1H, CH), 5.51–5.59 (m, 1H, vinylic H), 6.18–6.28 (m, 1H vinylic H), 6.37–6.48 (m, 1H, vinylic H), 8.10–8.28 (m, 1H, NH) ppm.

Preparation of the Polymeric Betaine Esters

VIII. Poly-N-(3-acrylamidopropyl)-N,N-dimethyl-N-(cis-3-hexenyloxycarbonyl)methylammonium chloride Homopolymerization in Water 16.7 g (0.05 mol) of the acrylamidoamine betaine ester II were weighed into a 250 ml four-necked flask fitted with stirrer, thermometer and reflux condenser under a nitrogen atmosphere. After the addition of 50 ml of distilled water, the mixture was heated to 90° C. to solowly and completely dissolve the betaine ester. When the reaction temperature was reached, 0.27 g (2 mol %) of potassium peroxodisulfate, dissolved in 2 ml of water, were added dropwise, with stirring, over a period of 1 h. The mixture was then stirred for an additional 2 h at 90° C. and then the water was distilled off in vacuo. 16.7 g of a pale yellow crystalline solid were obtained.

Homopolymerization in Isopropanol 14.42 g (0.041 mol) of the acrylamidoamine betaine ester II were weighed into a 250 ml four-necked flask fitted with stirrer, thermometer and reflux condenser under a nitrogen atmosphere. Following the addition of 13 g of isopropanol, the mixture was heated to 80° C. to slowly and completely dissolve the betaine ester and to form a single-phase mixture. When the reaction temperature was reached, 57 mg of AMBN (2,2' azobis-(2-methylbutyronitrile) dissolved in 0.92 g of isopropanol, were added dropwise, with stirring, over a period of 3 h. The mixture was then stirred for an additional hour at 80° C. Then, to complete the polymerization, 85 mg of AMBN, dissolved in 0.5 g of isopropanol, were added dropwise over a period of 30 minutes, and the mixture was stirred for a further 2 h at 80° C. After the solvent had been distilled off, 14.5 g of the homopolymer were obtained in the form of a pale yellow crystalline solid.

$^1$H-NMR (400 MHz, D$_2$O): δ=0.9–1.01 (m, 3H, CH$_3$), 1.25–1.90 (br, 3H, polymer chains-CH/CH$_2$), 1.91–2.14 (br, 4H), 2.42–2.54 (br, 2H), 2.88–2.98 (br, 2H), 3.10–3.24 (br, 6H, N(CH$_3$)$_2$), 3.57–3.72 (br, 2H, NCH$_2$), 4.24–4.44 (br, 4H, CH$_2$O and NCH$_2$C(O)), 5.34–5.46 (br, 1H vinylic H), 5.58–5.70 (br, 1H, vinylic H) ppm.

$^{13}$C-NMR (100.6 MHz, D$_2$O): δ=14.0 (br, 1C, CH$_3$), 20.4 (br, 1C), 22.8 (very broad, 1C), 25.2 (br, 1C), 26.1 (br, 1C), 36.0 (very broad, 1C), 42.0 (very broad, 1C), 50.8 (br, 2C, N(CH$_3$)$_2$), 61.1 (br, 1C, NCH$_2$), 63.7 (br, 1C, CH$_2$O), 65.6 (br, 1C NCH$_2$C(O)), 122.2 (br, 1C, CH=CH), 135.1 (br, 1C, CH=CH), 164.8 (br, 1C, ester C=O), 175.3 (br, 1C, amide CO) ppm.

IX. Poly-[N-(3-Acrylamidopropyl)-N,N-dimethyl-N-(cis-3-hexenyloxycarbonyl)methylammonium chloride-co-methyl acrylate]

Copolymerization in Isopropanol

Solutions of the acrylamidoamine betaine ester 11 (13.35 g, 0.04 mol in 27 g of isopropanol) and the free-radical initiator AMBN (40 mg in 5.2 g of methyl acrylate) were simultaneously added dropwise to 27 g of isopropanol in a 250 ml four-necked flask fitted with stirrer, thermometer and reflux condenser at 80° C. under a nitrogen atmosphere over a period of 80 min. Then, to complete the polymerization, an additonal 60 mg of AMBN, dissolved in 5 g of isopropanol, were added dropwise over a period of 30 minutes, and the mixture was stirred for a further 2 h at 80° C. After the solvent had been distilled off, 18.6 g of the copolymer were obtained in the form of a pale yellow crystalline solid.

$^1$H-NMR (400 MHz, CDCl$_3$): δ=0.95 (t, $^3J_{HH}$=7.54 Hz, 3H, CH$_3$), 1.22–1.96 (br, 3H, polymer chains-CH/CH$_2$), 2.02 (pseudo quintet, J$_{HH}$=7.44 Hz, 2H), 2.04–2.38 (br, 3H), 2.4 (m, br, 2H), 2.8–3.0 (br, 2H), 3.10–3.44 (br, 2H), 3.44–3.76 (br, 8H), 3.80–4.10 (br, 3H, OCH$_3$), 4.10–4.20 (br, 2H), 4.60–5.04 (br, 2H), 5.20–5.30 (br, 1H, vinylic H), 5.45–5.55 (br, 1H vinylic H) 8.0–9.0 (br, 1H, NH) ppm.

$^{13}$C-NMR (100.6 MHz, CDCl$_3$): δ=13.84 (1C, CH$_3$), 20.25 (1C), 22.7 (very broad, IC), 26.0 (br, 1C), 26.1 (br, 1C), 26,2 (br, 1C), 35.8 (very broad, 1C), 40.9 (very broad, 1C), 42.6 (very broad, 1C), 50.9 (br, 2C, N(CH$_3$)$_2$), 51.4 (br, 1C, OCH$_3$), 60.9 (br, 1C, NCH$_2$), 63.5 (br, 1C, CH$_2$O), 65.5 (br, 1C, NCH$_2$C(O)), 122.1 (br, 1C, CH=CH), 135.0 (br, 1C, CH=CH), 164.5 (br, 1C, ester C=O), 166.3 (br, 1C, ester C=O), 174.9 (br, 1C, amide CO) ppm.

X. Poly-N-(3-acrylamidopropyl)-N,N-dimethyl-N-(3,7-dimethyloct-6-en-1-oxycarbonyl)methylammonium chloride The homopolymer was prepared analogously to the synthesis (in isopropanol as solvent) of VIII.

$^{13}$C-NMR (100.6 MHz, CDCl$_3$): δ=17.6 (1C, CH$_3$), 19.2 (br, 1C), 23.0 (very broad, 2C), 25.2 (br, 1C), 25.6 (br, 1C), 29.4 (br, 1C), 35.0 (br, 1C), 36.3 (br, 1C), 36.8 (very broad, 1C), 43.0 (very broad, 1C), 51.0 (br, 2C, N(CH$_3$)$_2$), 61.3 (br, 1C, NCH$_2$), 64.0 (br, 1C, CH$_2$O), 65.1 (br, 1C, NCH$_2$C(O)), 124.2 (br, 1C, CH=CH), 131.3 (br, 1C, CH=CH), 164.9 (br, 1C, ester C=O), 175.7 (br, 1C, amide CO) ppm.

XI. Poly-[N-(3-Acrylamidopropyl)-N,N-dimethyl-N-(3,7-dimethyloct-6-en-1-oxycarbonyl)methylammonium chloride-co-methyl acrylate]

The copolymer was synthesized analogously to the preparation of IX.

Application Examples

For the performance assessment, hair tresses, which are used for sensory tests, were predamaged in a standardized manner by a permanent waving treatment and a bleaching treatment. Customary hairdressing products were used for this purpose.

Materials

- permanent waving liquid ("ondi", Wella)
- neutralizer ("neutrafix", Wella)
- bleaching powder ("blondor special", Wella)
- H$_2$O$_2$ ("Welloxyd 9%", Wella)
- shampoo without care component (sodium lauryl ether sulfate (12% washing-active substance, NaCl thickened)
- beakers
- hair coloring brush The treatment was carried out in the following order:

I. Permanent Waving Treatment

The hair tresses were moistened with the permanent waving liquid (weight ratio of hair: liquid=1:2). After a contact time of 15 minutes at room temperature in a covered beaker, the permanent waving liquid was carefully rinsed out for 2 min. The hair tresses were then gently pressed using a hand towel. The neutralizer (ratio of hair: liquid=1:2) had a contact time of 10 minutes at room temperature. The neutralizer was then carefully rinsed out for 2 minutes. The hair was then dried overnight at room temperature.

II. Bleaching Treatment

The bleaching powder and the H$_2$O$_2$ were formulated to give a paste (weight ratio of powder: H$_2$O$_2$=2:3). The paste was then immediately applied to the perm-treated hair using a brush. The contact time was 30 minutes at room temperature. The bleaching paste was then rinsed out under running water for 2 minutes. The hair was then washed with a shampoo without conditioner for 1 minute (amount of shampoo: 0.5 ml/hair tress) and then rinsed out for 1 minute. Before being used for the sensory tests, the predamaged hair tresses were dried overnight at room temperature.

Test Formulation

The conditioning products were tested in a simple hair rinse having the following composition:

| Product | Proportion by weight |
|---|---|
| Teginacid ® C (INCI: Ceteareth-25) | 0.5% |
| Tego ® Alkanol 16 (Cetyl Alcohol) | 2.0% |
| "Conditioner" | 2.0% |
| Water | ad. 100% |
| Citric acid | ad. pH 4.0 ± 0.3 |

® Trademark of Goldschmidt AG
"Conditioners" is the term used to refer to the products obtained in the preparation examples and comparative examples.

Standardized treatment of predamaged hair tresses with conditioning samples.

The hair tresses predamaged as described above were treated as follows with the above-described conditioning rinse:

The hair tresses were wetted under running warm water. The excess water was gently squeezed out by hand, then the rinse was applied and gently worked into the hair (1 ml/hair tress (2 g)). After a contact time of 1 minute, the hair was rinsed for 1 minute. Prior to the sensory assessment, the hair was dried in the air at 50% atmospheric humidity and 25° C. for at least 12 h.

Assessment Criteria

The sensory evaluations were made using grades given on a scale from 1 to 5, 1 being the poorest evaluation and 5 being the best evaluation.

| | Wet combability | |
|---|---|---|
| 5 | Coarse Toothing (of the comb) | No knots, the hair can be detangled easily. |
| | Fine Toothing | Very easy to comb through, no resistance detectable. |
| 4 | Coarse Toothing | Individual knots, slight resistance. |
| | Fine toothing | Easy to comb through, slight resistance detectable. |
| 3 | Coarse Toothing | A few knots, slight resistance. |
| | Fine Toothing | Some degree of resistance detectable, which decreases after repeated combing. |
| 2 | Coarse Toothing | Some knots, notable resistance. |
| | Fine Toothing | Notable resistance which does not decrease after repeated combing. |
| 1 | Coarse Toothing | Many knots, severe resistance. |
| | Fine Toothing | Very severe resistance, sometimes the hair cannot be combed through. |

| | Wet feel |
|---|---|
| 5 | Very smooth, soft but nevertheless beautifully strong, of good feel, not greasy/tacky (no residues detectable) |
| 4 | Smooth and soft and/or only slight residues detectable |
| 3 | Smooth, somewhat hard and/or some residues detectable |
| 2 | Hard and/or notable greasy, waxy residues |

-continued

Wet feel

| | |
|---|---|
| 1 | Very hard, rough, harsh and/or extremely greasy, tacky (clearly detectable greasy, waxy residues detectable) |

Dry combability

| | | |
|---|---|---|
| 5 | coarse toothing | No knots, the hair can be detangled easily |
| | fine toothing | Very easy to comb through, no resistance detectable, the hair does not become charged |
| 4 | coarse toothing | Individual knots. The hair can be detangled easily |
| | fine toothing | Easy to comb through, no resistance detectable, the hair becomes charged to a minimum degree |
| 3 | coarse toothing | A few knots, slight resistance |
| | fine toothing | Some resistance detectable which decreases after repeated combing, the hair becomes slightly charged |
| 2 | coarse toothing | Some knots, notable resistance |
| | fine toothing | Notable resistance which does not decrease after repeated combing, the hair becomes charged |
| 1 | coarse toothing | Many knots, severe resistance |
| | fine toothing | Very severe resistance, sometimes the hair cannot be combed through, the hair becomes considerably charged |

Dry feel

| | |
|---|---|
| 5 | Very smooth, soft but nevertheless strong, full, of good feel |
| 4 | Smooth and soft |

Dry appearance

| | |
|---|---|
| 5 | Extremely shiny |
| 4 | Shiny |
| 3 | Somewhat shiny |
| 2 | Slightly shiny, slightly harsh |
| 1 | Harsh, no shine |

Volume

In order to assess the volume, the hair locks were shaken gently by holding them at the bonding point.

| | |
|---|---|
| 5 | Loose, bulky drop, Ø (i.e., diameter) in the tip area rel. large |
| 4–2 | Intermediate stages |
| 1 | Hair hangs heavily downward, Ø below the bundling similar to the tip area |

To determine the electrostatic behavior of the hair tresses, a "fly-away test" was carried out. Here, the transfer of electric charge to a hair tress by combing was determined. The splaying out of the hair tresses as a result of electrostatic proportion of the hairs among one another was measured. For comparison, this measured value for each conditioning agent was given relative to the measured value for the control sample (reduction in splaying out relative to the control sample).

In the table below the results of the sensory assessment of the treatment of hair tresses carried out as described above with compounds according to the invention and comparative examples were compared.

| Test formulation with example compound | Odor/fragrance | Detangling wet | Wet combability | Wet feel | Dry combability | Dry feel | Shine | Volume | Reduction in the "fly-away effect" |
|---|---|---|---|---|---|---|---|---|---|
| Preparation example XI (citronellol) | 4 | 4.5 | 4 | 4 | 2.25 | 2.4 | 1.75 | 2.5 | −8 |
| Preparation example stearyl betaine ester copolymer | 3 | 3 | 3.25 | 3.75 | 4.75 | 3.5 | 3.5 | 2.75 | 12 |
| Preparation example ethyl betaine ester copolymer | 3 | 3.75 | 3.25 | 3 | 3.5 | 3 | 4 | 3.5 | −252 |
| Preparation example V lauryl-PEG9-betaine ester copolymer | 3 | 4 | 3.5 | 3.75 | 3 | 4 | 4.5 | 3.25 | 22 |
| Comparative example cetrimonium chloride (industry standard) | 3 | 5 | 5 | 5 | 5 | 4.5 | 4.5 | 2.5 | 78 |
| Control | 3 | 2.25 | 1.75 | 1.5 | 3.5 | 2.25 | 3 | 3 | (def. =) 0 |

-continued

Dry feel

| | |
|---|---|
| 3 | Smooth, slightly hard and/or slightly harsh (residues) |
| 2 | Hard, somewhat harsh |
| 1 | Rough, hard, dry, harsh (residues) |

It is found that the compounds according to the present invention provided good conditioning properties, some of which correspond to those of the industry standard Cetrimonium Chloride, and achieved considerably better evaluations compared with the polyether-free aminosiloxanes in the sensory assessment. In evaluation of odor, only the preparation example XI was evaluated as being better than all of the comparative examples.

While the present invention has been particularly shown and described with respect to preferred embodiments thereof, it will be understood by those skilled in the art that the foregoing and other changes in forms and details may be made without departing from the spirit and scope of the present application. It is therefore intended that the present invention is not limited to the exact forms and details described and illustrated, but fall within the scope of the appended claims.

What we claim is:

1. An oligomeric or polymeric compound prepared by copolymerization of from 0.5 to 100 mol % of a polymerizable betaine ester of claim 1; and 0 to 99.5 mol % of an ethylenically unsaturated comonomer of general formula (II)

in which

R$^x$ and R$^y$ are H, R$^w$ is H or CH$_3$ and R$^z$ is a radical —C(O)OR, —C(O)NR'R" containing at least one carbonyl group, where R, R' and R" are H or hydrocarbon radicals having 1 to 18 carbon atoms.

2. An oligomeric or polymeric compound of claim 1 wherein from 20 to 70 mol % of said polymerizable betaine ester of general formula (I) and 30 to 80 mol % of said unsaturated comonomer of general formula (II) are employed.

3. An oligomeric or polymeric compound of claim 1 wherein from 40 to 60 mol % of said polymerizable betaine ester of general formula (I) and 60 to 40 mol % of said ethylenically unsaturated comonomer of general formula (II) are employed.

4. A polymeric compound as claimed in claim 1 comprising, as comonomers, compounds of formula (II) wherein R$^w$ and R$^x$ are H, R$^y$ and R$^z$ are radicals —C(O)OR, —C(O)NR'R" containing a carbonyl group, where R, R' and R" are H or hydrocarbon radicals having 1 to 18 carbon atoms.

5. A polymeric compound as claimed in claim 1 comprising, as comonomers, compounds of formula (II) wherein R$^w$, R$^x$ and R$^y$ are H and R$^z$ is an alkyl substituent-containing aromatic or heteroaromatic substituents.

6. A polymeric compound as claimed in claim 1 comprising, as comonomers, compounds of formula (II) wherein R$^w$, R$^x$ and R$^y$ are H and R$^z$ is —(CH$_2$)$_a$—OR'", where R'" is H or an alkyl radical having 1 to 22 carbon atoms or is a polyether derived exclusively from ethylene oxide or propylene oxide or butylene oxide or styrene oxide, which represents a block or random copolymer containing said radicals, and a is 0 or 1.

7. A polymeric compound as claimed in claim 1 comprising, as comonomers, at least one compound selected from the group C$_1$–C$_{18}$-acrylic esters, methacrylic esters or maleic mono- or diesters,;

polyethylene glycol and polypropylene glycol acrylates and methacrylates;

C$_2$–C$_{18}$-alkoxy esters of acrylic and methacrylic acid;

C$_2$–C$_8$-hydroxyalkyl acrylates and methacrylates;

vinyl compoundsvinyl esters, vinyl ethers, halogenated vinyl compounds, allyl vinyl ketone, 4-vinylpridine, N-vinylpyrrolidone, vinylimidazole;

amides of acrylic acid and methacrylic acid; diallyldimethylammonium chloride (DADMAC); and allyl compounds.

* * * * *